(12) United States Patent
Dobashi (10) Patent No.: US 8,591,028 B2
(45) Date of Patent: Nov. 26, 2013

(54) OPHTHALMOLOGIC PHOTOGRAPHING APPARATUS AND PHOTOGRAPHING METHOD THEREFOR

(75) Inventor: Yasuhiro Dobashi, Matsudo (JP)

(73) Assignee: Canon Kabushiki Kaisha, Tokyo (JP)

( * ) Notice: Subject to any disclaimer, the term of this patent is extended or adjusted under 35 U.S.C. 154(b) by 250 days.

(21) Appl. No.: 12/857,748

(22) Filed: Aug. 17, 2010

(65) Prior Publication Data
US 2011/0051084 A1    Mar. 3, 2011

(30) Foreign Application Priority Data

Aug. 27, 2009 (JP) ................. 2009-196999

(51) Int. Cl.
*A61B 3/14*    (2006.01)
(52) U.S. Cl.
USPC .................. 351/206; 351/221; 351/246
(58) Field of Classification Search
USPC .......................... 351/206, 221, 246
See application file for complete search history.

(56) References Cited

U.S. PATENT DOCUMENTS 5,118,179 A * 6/1992 Sano et al. ............... 351/206
2010/0097574 A1 4/2010 Kushida

FOREIGN PATENT DOCUMENTS

JP          9-66030 A     3/1997
JP     2004-180705 A     7/2004

* cited by examiner

*Primary Examiner* — Hung Dang
(74) *Attorney, Agent, or Firm* — Canon USA Inc. IP Division (57) ABSTRACT

An ophthalmologic photographing apparatus includes an illumination unit configured to illuminate a subject's eye with one of infrared light and visible light, an input unit configured to input a signal to the illumination unit, a measurement unit configured to measure an input time of the signal from the input unit, a detection unit configured to detect that the input time is a predetermined time or longer, and a control unit configured to control the illumination unit according to a detection result by the detection unit to switch from the infrared light to the visible light.

20 Claims, 10 Drawing Sheets

| No. | NAME OF SUBJECT | PHOTOGRAPHY MODE | OBSERVATION LIGHT SOURCE | MYDRIATIC INSTILLED /NOT-INSTILLED |
|---|---|---|---|---|
| 1 | ICHIRO CANON | FA PHOTOGRAPHY | INFRARED LIGHT OBSERVATION | INSTILLED |
| 2 | JIRO CANON | COLOR PHOTOGRAPHY | VISIBLE LIGHT OBSERVATION | INSTILLED |
| 3 | HANAKO CANON | COLOR PHOTOGRAPHY | INFRARED LIGHT OBSERVATION | NOT-INSTILLED |
| | | | | |

OPHTHALMOLOGIC PHOTOGRAPHING APPARATUS AND PHOTOGRAPHING METHOD THEREFOR

BACKGROUND OF THE INVENTION

1. Field of the Invention

The present invention relates to an ophthalmologic photographing apparatus capable of switching between an infrared light observation and a visible light observation, and a photographing method therefor.

2. Description of the Related Art

Known methods of fundus photography include non-mydriatic photography of photographing a fundus without a mydriatic instilled into a subject's eye, and mydriatic photography of photographing a fundus with a mydriatic instilled into a subject's eye. In the non-mydriatic photography, a fundus is photographed while a subject's eye is in a state of natural mydriasis in a dark place, and generally, an observation is made with use of infrared light to prevent miosis of a subject's eye from occurring during an observation.

On the other hand, in the mydriatic photography, a fundus is photographed while a subject's eye is forced into a mydriasis state by a mydriatic. Therefore, miosis does not occur even if visible light is projected on a subject's eye, and generally, an observation is made with use of visible light. However, in some cases, an observation may be made with use of infrared light to reduce a burden on a subject's eye.

Japanese Patent Application Laid-Open No. 9-66030 discusses an ophthalmologic photographing apparatus that can be used for both the non-mydriatic photography and the mydriatic photography. In this apparatus, an operator can switch between the non-mydriatic photography function and the mydriatic photography function, and an infrared light observation is performed during the non-mydriatic photography and a visible light observation is performed during the mydriatic photography.

Fluorescence photography, in which a subject's eye is photographed with a fluorescent agent intravenously injected into the body of the subject, requires an examination time of normally 10 to 30 minutes or longer. During an early stage of fluorescence, since the amount of a change in an observed image due to an inflow of the fluorescent agent is large, a number of photographs are taken in a short time. However, during a later stage of fluorescence, since the fluorescent agent has been circulated throughout the eye fundus and, therefore, the amount of a change in an observed image is small, a photographing interval is increased. When there are many subjects to be photographed, another subject may be photographed by utilizing an idle time during the first subject's photographing interval in the later stage of fluorescence, in order to improve the overall photographing efficiency.

As an apparatus that can be used in such a case, Japanese Patent Application Laid-Open No. 2004-180705 discusses an apparatus that can simultaneously implement a plurality of examinations.

However, an operator may forget to switch from the visible light observation to the infrared light observation, when a subject to be now examined is changed from a person who has undergone a visible light observation with a mydriatic instilled into his/her eye, to a person who is about to undergo an infrared light observation without a mydriatic instilled into his/her eye. Further, when a subject's eye without a mydriatic instilled therein is observed with use of infrared light, an operator may switch from the infrared light observation to the visible light observation by an operational mistake.

In such a case, when visible light is projected to a subject's eye without a mydriatic instilled therein, the subject' eye becomes miotic. Once the subject's eye becomes miotic, a waiting time may be required until the subject's eye naturally becomes mydriatic, and, therefore, the photographing efficiency is impaired.

On the other hand, since daily operations habituate an operator to a certain extent, if an apparatus requires a special operation to an operator only for a part of functions thereof, the operator may have an uncomfortable feeling to the operation of the apparatus, which may result in an induction of an operational mistake.

SUMMARY OF THE INVENTION

The present invention is directed to an ophthalmologic photographing apparatus capable of preventing projection of visible light by an operator's operational mistake to a subject' eye without a mydriatic instilled therein which should be observed with infrared light, thereby preventing miosis of the subject's eye.

According to an aspect of the present invention, an ophthalmologic photographing apparatus includes an illumination unit configured to illuminate a subject's eye with one of infrared light and visible light, an input unit configured to input a signal to the illumination unit, a measurement unit configured to measure an input time of the signal from the input unit, a detection unit configured to detect that the input time is a predetermined time or longer, and a control unit configured to control the illumination unit according to a detection result by the detection unit to switch from the infrared light to the visible light.

According to another aspect of the present invention, an ophthalmologic photographing method includes measuring an input time of a signal input into an illumination unit configured to illuminate a subject's eye with one of infrared light and visible light, and controlling the illumination unit according to a result of detection that the input time is a predetermined time or longer to switch from the infrared light to the visible light.

According to an ophthalmologic photographing apparatus according to an exemplary embodiment of the present invention, upon detection that the input unit (observation light changeover switch) is kept pressed for a predetermined time or is pressed multiple times within the predetermined time, the observation light is switched from infrared light to visible light. Due to this arrangement, it becomes possible to prevent projection of visible light by an operator's operational mistake to a subject' eye without a mydriatic instilled therein which should be observed with infrared light, thereby preventing miosis of the subject's eye.

Further, an issue of a warning in advance indicating that the observation light is to be switched can give an operator a certain time to recheck the situation, thereby preventing projection of visible light to a subject's eye by an operator's operational mistake.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

DESCRIPTION OF THE EMBODIMENTS

Various exemplary embodiments, features, and aspects of the invention will be described in detail below with reference to the drawings.

Figure 1:
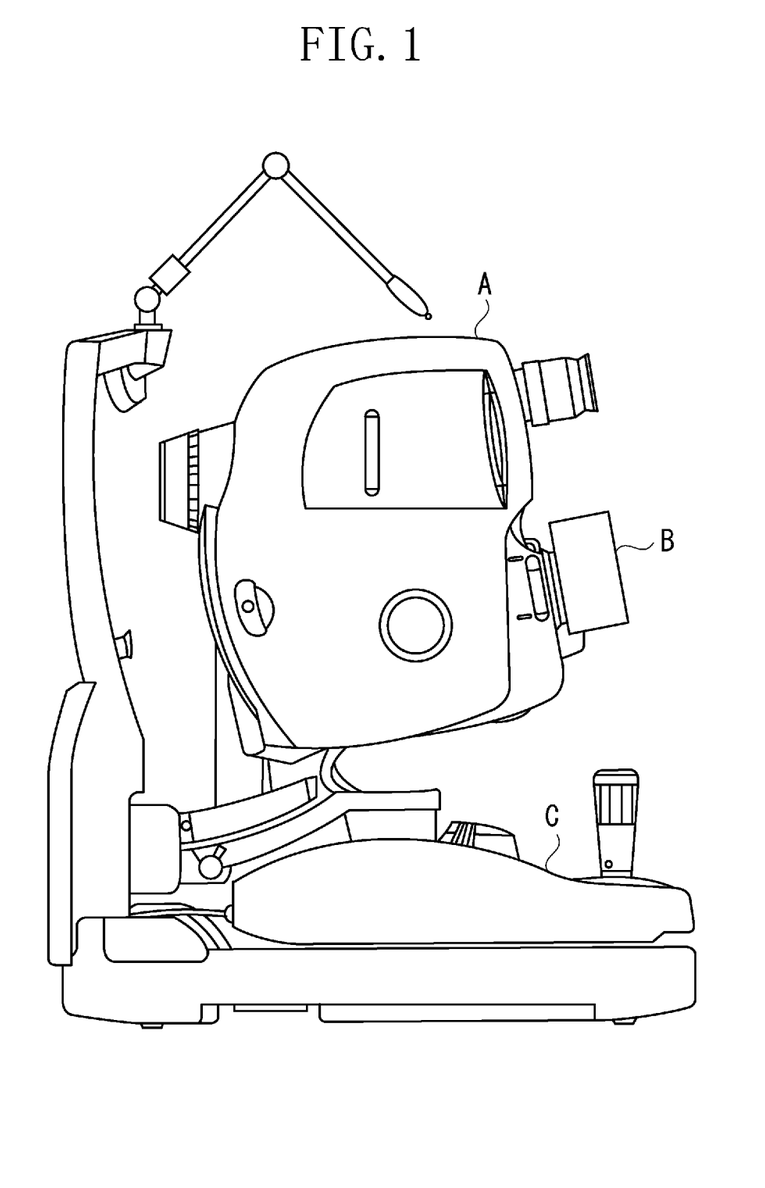
FIG. 1 illustrates an outer appearance of an ophthalmologic photographing apparatus according to a first exemplary embodiment of the present invention.

FIG. 1 illustrates an outer appearance of an ophthalmologic photographing apparatus according a first exemplary embodiment of the present invention. A camera body B including a liquid crystal monitor is attached to a fundus camera unit A, and an operation panel C is disposed on a base of the ophthalmologic photographing apparatus.

Figure 2:
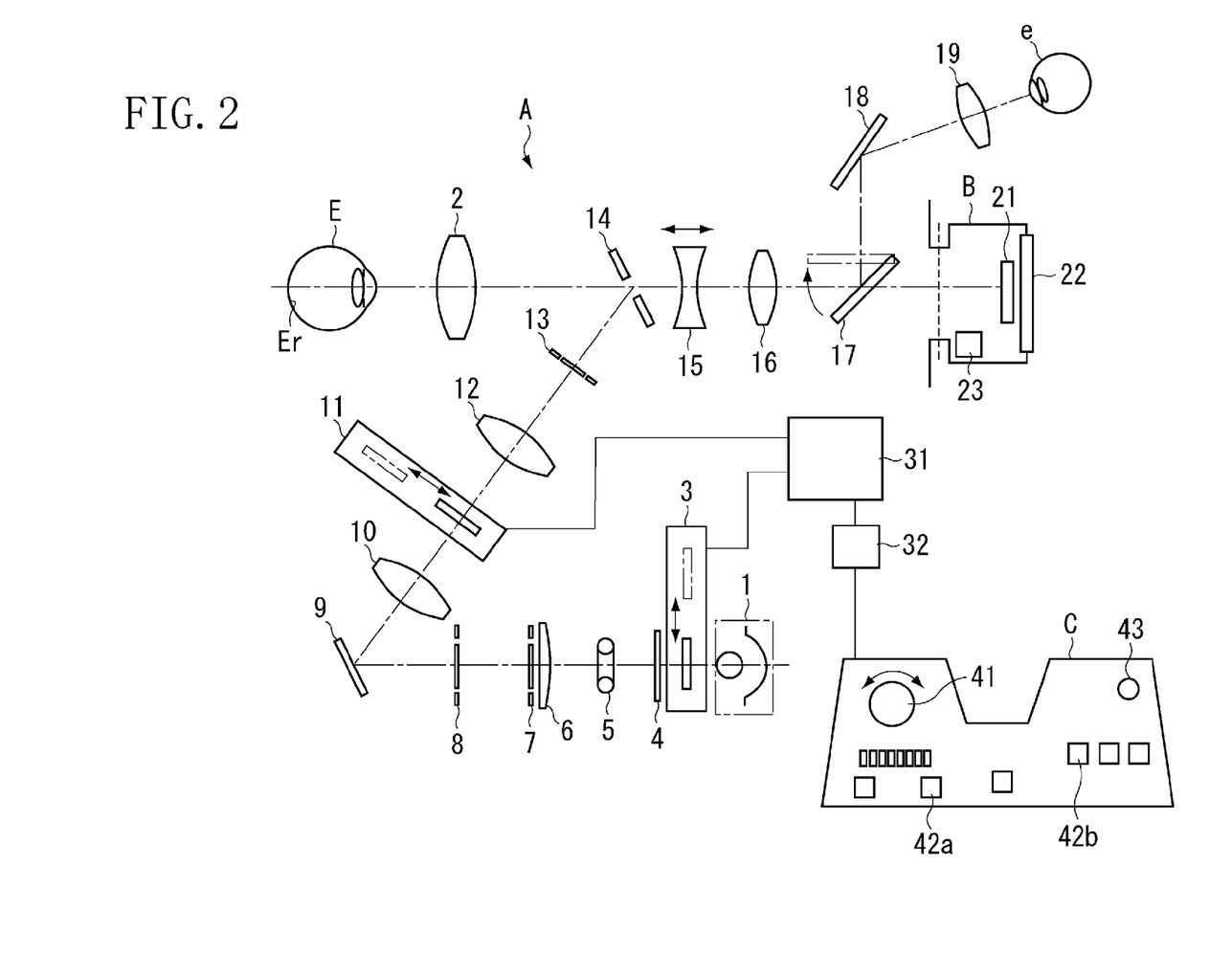
FIG. 2 illustrates an optical and electrical configuration of the ophthalmologic photographing apparatus.

FIG. 2 illustrates an optical and electrical configuration of the ophthalmologic photographing apparatus. A visible light cut filter 3, a diffusion plate 4, an observation light source 5 such as a flash tube, a condenser lens 6, a pupil stop 7, a crystalline lens stop 8, and a folding mirror 9 are arranged in this order in the optical path of a fundus illumination optical system from an observation light source 1 to an objective lens 2 facing a subject's eye E. A relay lens 10, an infrared light cut filter 11, a relay lens 12, a cornea stop 13, and a perforated mirror 14 are arranged in this order in the reflecting direction of the folding mirror 9.

The visible light cut filter 3 and the infrared light cut filter 11 can be retracted from and inserted into the optical path. The retraction and insertion of the visible light cut filter 3 and the infrared light cut filter 11 are controlled such that the visible light cut filter 3 and the infrared light cut filter 11 have reversed retraction/insertion states to each other. Therefore, when the visible light cut filter 3 is positioned in the optical path, i.e., when the infrared light cut filter 11 is retracted to the outside of the optical path, a fundus Er is illuminated by infrared light. On the other hand, when the infrared light cut filter 11 is positioned in the optical path, i.e., when the visible light cut filter 3 is retracted to the outside of the optical path, the fundus Er is illuminated by visible light.

A fundus observation optical system is disposed in the optical path in the transmission direction of the perforated mirror 14. A focusing lens 15 movable in the optical axial direction, a photographic lens 16, a flip-up mirror 17, and the camera body B are arranged in this optical path. A mirror 18 and an eyepiece lens 19 are arranged in the reflecting direction of the flip-up mirror 17.

The camera body B includes an image sensor 21, a liquid crystal monitor 22, and an image transfer unit 23 for outputting an image to an external monitor. As the camera B, this ophthalmologic photographing apparatus can use multiple kinds of cameras such as a digital single lens reflex camera, and any camera having the same optical focal length and the same mount structure can be attached thereto.

Further, a system control unit 31 is mounted in the ophthalmologic photographing apparatus, and the output of the system control unit 31 is connected to the visible light cut filter 3 and the infrared light cut filter 11. Further, the operation panel C is connected to the system control unit 3 via an input detection unit 32.

The operation panel C includes, for example, a potentiometer 41 for setting an observation light amount at the time of a fundus observation, a control switch 42a for determining a light emission amount of the observation light source 5 at the time of fundus photography, and a mode switch 42b for determining various photography conditions such as fluorescence photography and color photography. The operation panel C includes the switches 42a, 42b . . . of the number corresponding to the number of the settings. Further, the operation panel C includes an observation light changeover switch 43, since an operator can select visible light or infrared light as observation light at this ophthalmologic photographing apparatus. In the present exemplary embodiment, the observation light changeover switch 43 is referred to as "first input unit", and the other switches are referred to as "second input unit".

Since the first input unit and the second input unit are disposed at the same operation panel C, it is structurally difficult to prepare switches providing extremely different operational feeling. Further, in consideration of the possibility that the functions assigned to the switches may be changed when the operation unit is diverted to a different machine model, all of the input units are embodied by the same type of switch. Further, in the present exemplary embodiment, an input at the operation panel C is performed with use of mechanical switches, but the switches may be constituted by soft switches on a touch panel with use of a liquid crystal panel.

A fundus image reflected at the fundus Er of the subject's eye E is guided to an examiner's eye e via the mirror 18 and the eyepiece lens 19 at the time of an visible light observation, or is guided to the image sensor 21 inside the camera body B due to flipping-up of the flip-up mirror 17 as indicated by the dotted line at the time of an infrared light observation. The fundus image guided to the image sensor 21 at the time of an infrared light observation is transferred to and displayed at the liquid crystal monitor 22, or at the not-shown external monitor via the image transfer unit 23.

Figure 3:
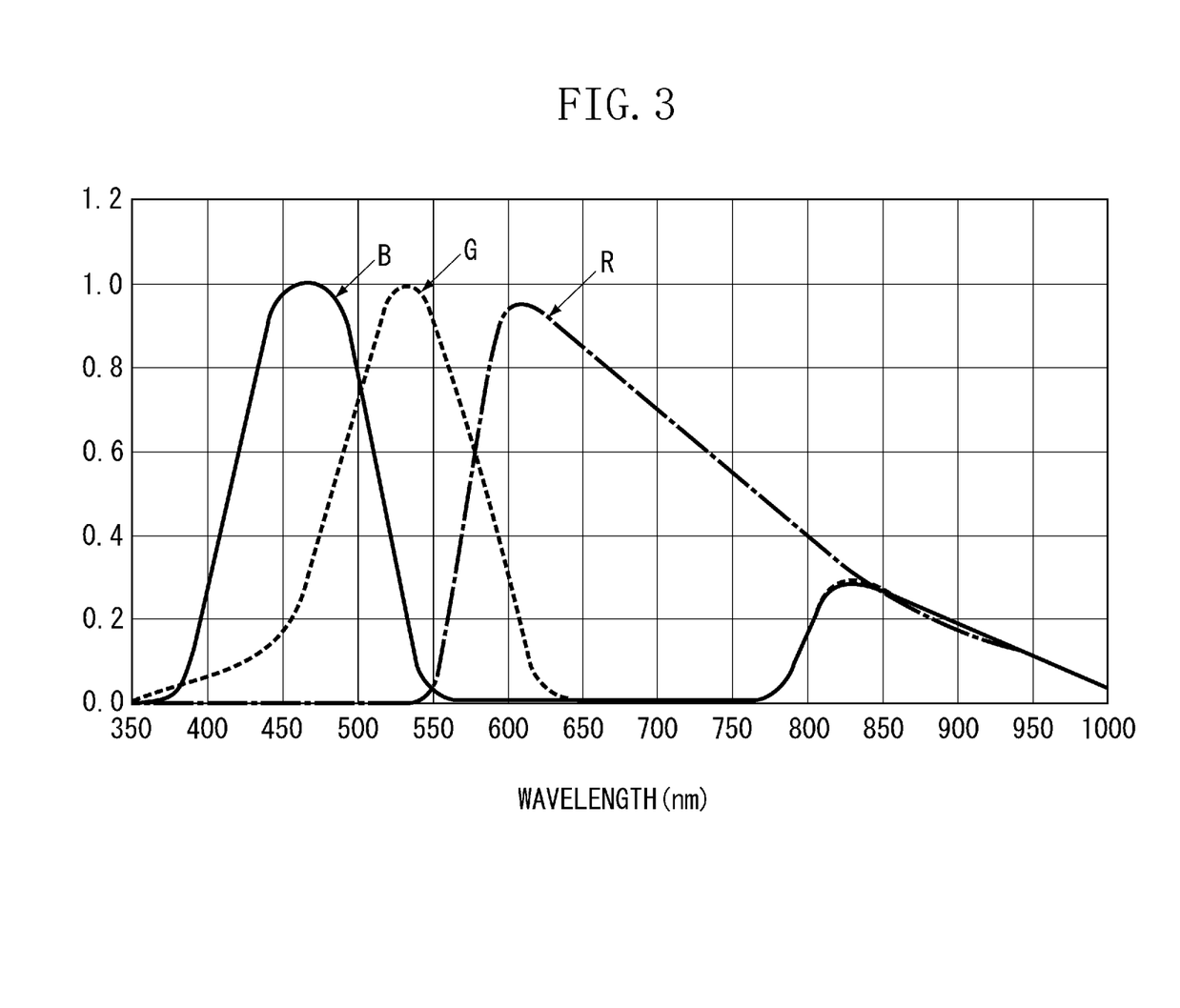
FIG. 3 illustrates a spectral sensitivity characteristic of an image sensor.

FIG. 3 illustrates the spectral sensitivity characteristic of the image sensor 21. As illustrated in FIG. 3, the image sensor 21 has sufficient sensitivity characteristic to the visible region and infrared region, and, therefore, can be used as both of an infrared light observation unit and a visible light observation unit. Both of a visible light observation image and an infrared light observation image can be captured by the image sensor 21. Therefore, even at the time of a visible light observation, an image can be observed via the liquid crystal monitor 22 or the external monitor by flipping up the flip-up mirror 17 to the position indicated by the dotted line, as is the case with an infrared light observation.

It can be assumed that the subject's eye E at the time of an infrared light observation is in a mydriasis state with a mydriatic instilled therein or is in a non-mydriasis state without a mydriatic instilled therein. If a mydriatic is instilled into the subject's eye, miosis does not occur even when visible light is projected to the subject's eye E. However, some subjects may come to blink more rapidly by being affected by the dazzle of visible light, and may have difficulty in maintaining the visual fixation. Therefore, generally, some operators take into consideration the influence to the subject's eye E, and perform a fundus observation with use of infrared light even when a mydriatic is instilled into the subject's eye E.

Figure 4:
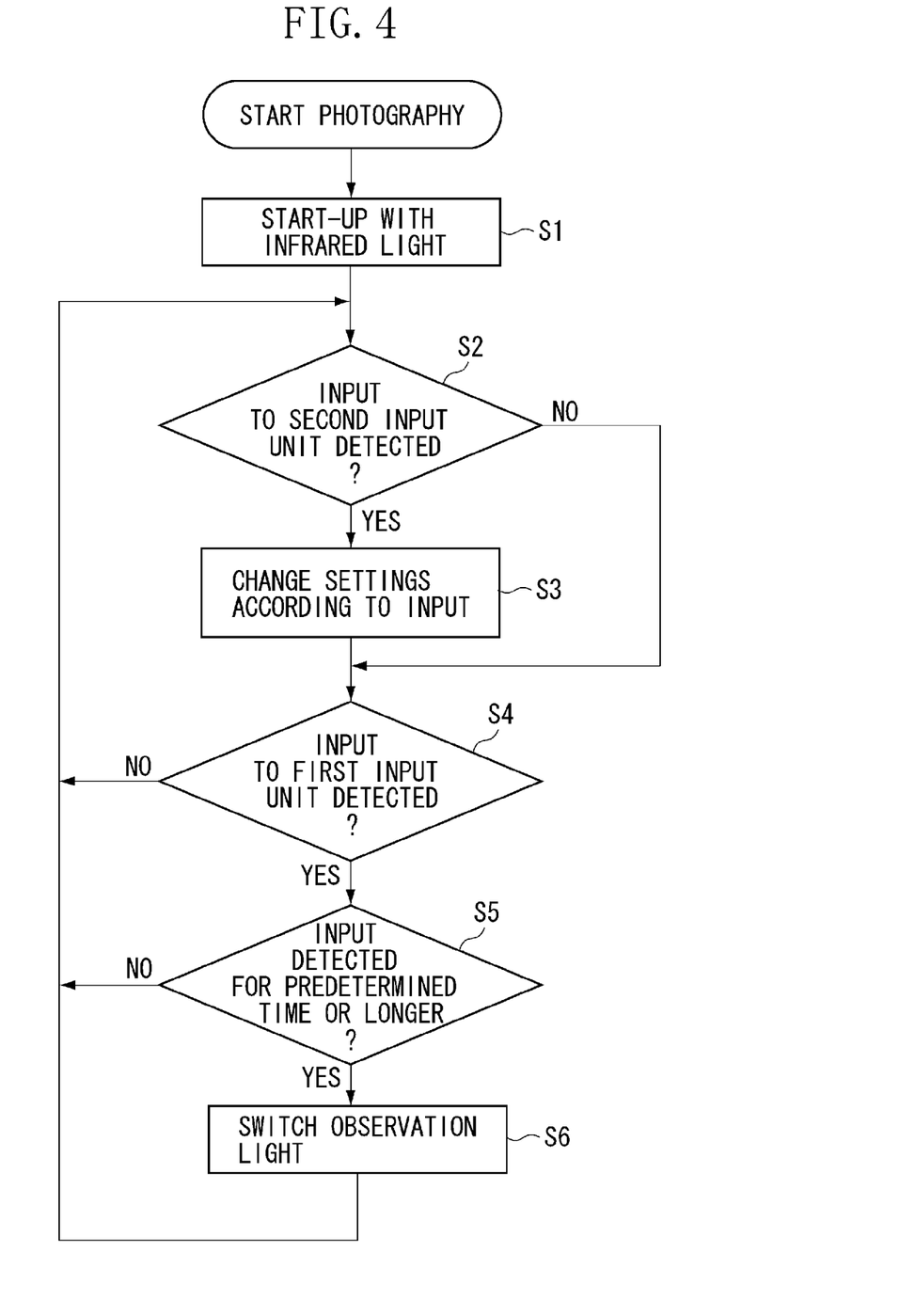
FIG. 4 is an operational flowchart of the ophthalmologic photographing apparatus according to the first exemplary embodiment.

FIG. 4 is an operational flowchart. When photography is started, in step S1, an observation is performed with use of infrared light as observation light at the time of a system startup regardless of the mydriasis state of the subject's eye, since an unexpected situation such as misidentification of the subject or forgetting to instill a mydriatic into the subject's eye E should be prepared for. At this time, in the illumination optical system, the system control unit 31 inserts the visual light cut filter 3 into the optical path, and retracts the infrared right cut filter 11 to the outside of the optical path, since the illumination light at the time of the observation has the near-infrared wavelength. Further, the system control unit 31 causes the flip-up mirror 17 to be flipped up to the position indicated by the dotted line, and thereby the fundus image of the subject's eye E to be guided to the image sensor 21.

The operator performs position adjustment and focus adjustment to the fundus Er by operating the stage unit on which the optical system is disposed, while observing the infrared light observation image output from the image sensor 21 via the liquid crystal monitor 22 or the external monitor.

Next, in step S2, the input detection unit 32 detects whether, for example, the switches 42a and 42b, which are the second input unit on the operation panel C, are operated. If the operator operates the second input unit (YES in step S2), then the processing proceeds to step S3. In step S3, the system control unit 31 immediately sets, for example, a photography light amount and supply/retraction of a not-shown photography index based on the input information obtained in step S2, and maintains the observation state.

If the input detection unit 32 cannot detect an operation to the second input unit in step S2 (NO in step S2), i.e., if the initial settings are maintained for the photography, then the processing proceeds to step S4.

Generally, fundus photography is carried out in a dark room to prevent miosis of the subject's eye E. Further, since the operator operates the operation panel C while performing alignment and focus adjustment to the subject's eye E, the operator may accidentally operate the observation light changeover switch 43, which is the first input unit, when the operator actually intends to operate the second input unit such as the switches 42a and 42b.

Next, in step S4, the input detection unit 32 detects an operation to the observation light changeover switch 43, which is the first input unit, and determines whether the operator actually wants to switch the observation light. If observation light switching information is input from the first input unit (YES in step S4), the processing proceeds to step S5. In step S5, the system control unit 31 detects whether an input is applied to the switch for a predetermined time set in advance or longer. If it is determined that an input is applied to the switch for the predetermined time or longer (YES in step S5), then the processing proceeds to step S6. In step S6, the system control unit 31 switches the observation light.

If an operation at the first input unit cannot be detected in step 4 (NO in step S4), or an input at the switch for the predetermined time or longer cannot be detected in step 5 (NO in step S5), the processing returns to step S2 without the system control unit 31 switching the observation light.

As used herein, the predetermined time is defined as a time sufficiently long to enable detection that the operator intentionally performs an operation different from the operation at the other operation input units, including "keeping the switch pressed for a predetermined time (long pressing)" and "pressing the switch multiple times within a predetermined time". Usually, for the system control unit 31's detection of an input to a switch, a time of approximately several tens of milliseconds is employed for detection of an input in order to avoid influence of chattering of the switch generated when the switch is turned on or off.

In the present exemplary embodiment, the detection time for the second input unit is set as approximately several tens of milliseconds, while the detection time for the first input unit is set as several hundred milliseconds, which is sufficiently longer than the detection time for the second input unit. It can be determined whether the first input unit is pressed down by an operational mistake or intentionally, by detecting the operator' operation for or within the predetermined time.

On the other hand, for example, when the operator wants to observe a subject's eye E with a mydriatic instilled therein with visible light through the eyepiece lens 19, or when the operator starts to observe a subject's eye E with a mydriatic instilled therein after observing another subject's eye E without a mydriatic instilled therein, the observation light should be switched from infrared light to visible light. In such a case, the operator long-presses the first input unit or presses the first input unit multiple times within the predetermined time. Due to this operation, the input detection unit 32 determines in step S5 that the first input unit is operated for the predetermined time or longer, and then notifies the system control unit 31 of the switching information. In step S6, the system control unit 31 switches the observation light source.

At the time of a visible light observation, in the fundus illumination optical system, the system control unit 31 retracts the visual light cut filter 3 to the outside of the optical path, and inserts the infrared right cut filter 11 into the optical path to prevent infrared light unnecessary to the visible light observation from being projected to the fundus Er, since the illumination light at the time of the observation has the visible wavelength. At the time of this visible light observation, the system control unit 31 causes the flip-up mirror 17 to be inserted in the optical path so that the operator can directly observe the fundus image through the eyepiece lens 19. Alternatively, as is the case with an infrared light observation, the system control unit 31 causes the flip-up mirror 17 to be flipped up to the position indicated by the dotted line, and thereby the fundus image of the subject's eye E to be guided to the image sensor 21, enabling a visible light observation via the liquid crystal monitor 22 or the external monitor.

Figure 5:
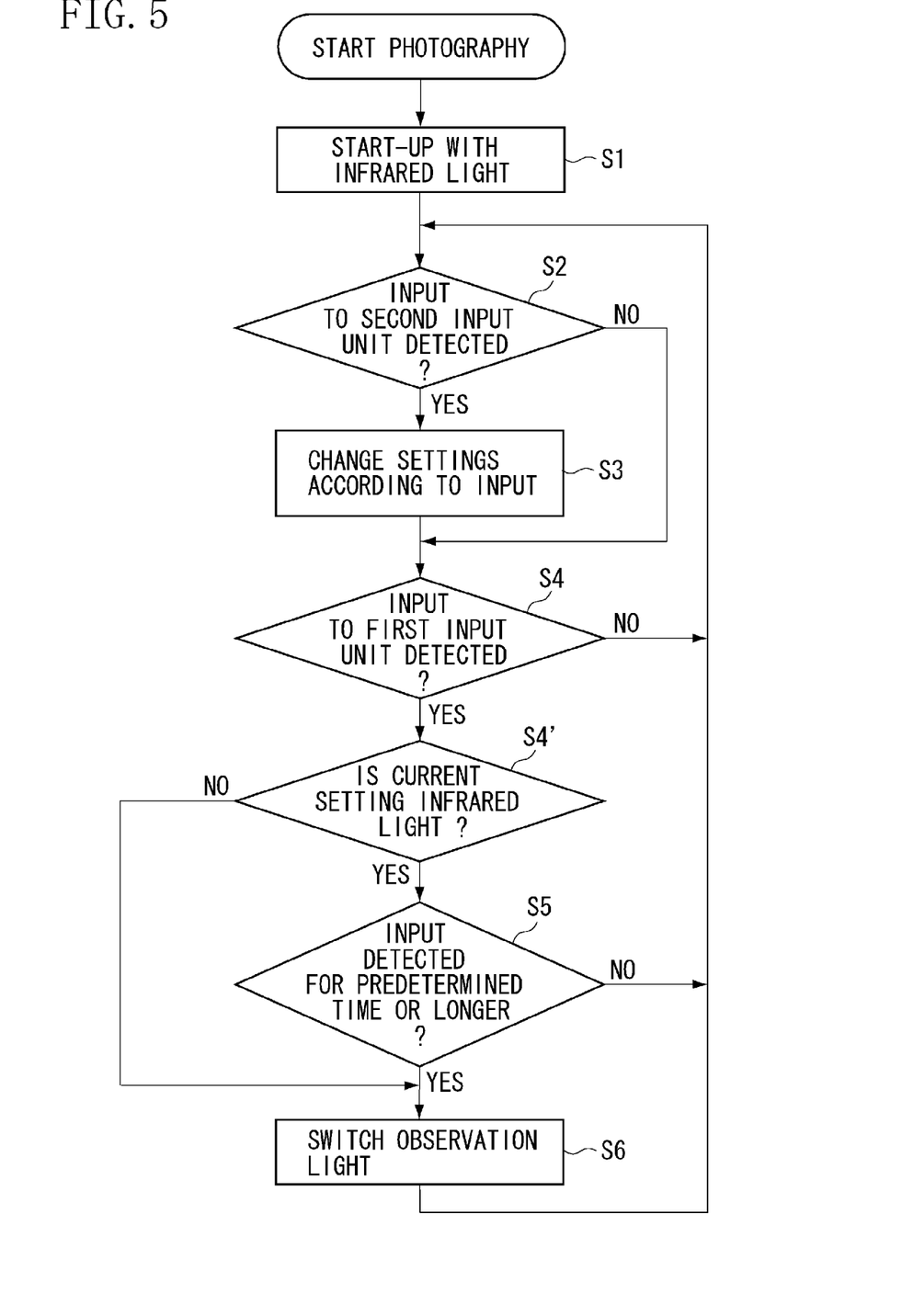
FIG. 5 is an operational flowchart of the ophthalmologic photographing apparatus according to the first exemplary embodiment.

FIG. 5 is a operational flowchart illustrating a method for switching the observation light from visible light to infrared light when an operator observes a subject's eye E with a mydriatic instilled therein with use of infrared light, or when an operator starts to observe a subject's eye E without a mydriatic instilled therein after observing another subject's eye with a mydriatic instilled therein, conversely to the above-mentioned example. In FIG. 5, the same operations are identified by the same step numbers as in FIG. 4, and will not be repeatedly described below.

The operational flowchart illustrated in FIG. 5 includes step S4' newly added thereto. The system control unit 31 is configured such that, in step S4', the system control unit 31 detects whether the current observation light setting is the infrared light or the visible light, and switches the observation light in response to long-pressing of the switch or multiple operations of the switch only when the observation light is switched from infrared light to visible light.

Since miosis of the subject' eye E does not occur when the observation mode is switched from the visible light observation to the infrared light observation, actually, the determination in step S5 is unnecessary. However, if an operator, at the time of switching the observation light, has to operate the first input unit in different manners between switching from infrared light to visible light and switching from visible light to infrared light, the operator may have an uncomfortable feeling to the operation, which may induce a mistake in operating the apparatus. Therefore, in the present first exemplary embodiment, for switching the observation light, the switch should be long-pressed regardless of whether miosis occurs, so that uniformity of operability can be maintained.

Since miosis of the subject' eye E does not occur when the observation mode is switched from the visible light observation to the infrared light observation, in this case, the detection time for the first input unit in step S5 is changed to be the same as the detection time for the second input unit. Due to this arrangement, at the time of switching the observation light, the operator does not have to operate the first input unit for or within the predetermined time set in the first exemplary embodiment, and can switch the observation light by operating the first input unit in a similar manner to the operation of the second input unit.

However, if the operator agrees and determines in advance that long-pressing of the switch is unnecessary for switching "from the visible light observation to the infrared light observation", the system may be changed.

In this way, at the time of switching the observation light, the first input unit should be long-pressed or operated multiple times, whereby it is possible to prevent visible light from being projected to a subject's eye E without a mydriatic instilled thereto by an operational mistake of an operator, and to prevent a time loss at the time of photography due to miosis of the subject's eye E.

Figure 6:
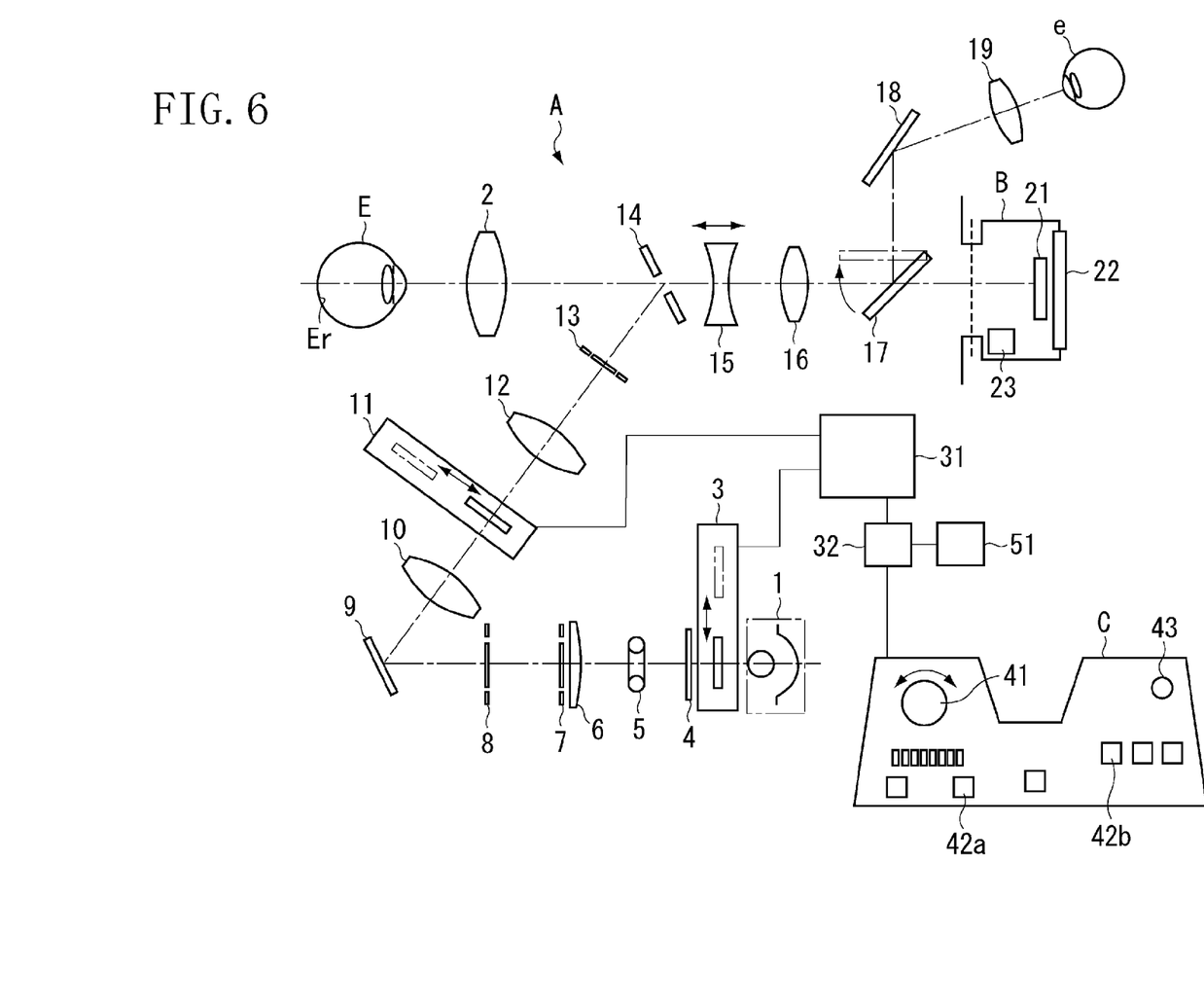
FIG. 6 illustrates an optical and electrical configuration of an ophthalmologic photographing apparatus according to a second exemplary embodiment of the present invention.

FIG. 6 illustrates an optical and electrical configuration of an ophthalmologic photographing apparatus according to a second exemplary embodiment of the present invention. The second exemplary embodiment is different from the first exemplary embodiment in terms that, in the second exemplary embodiment, a third input unit 51 for inputting information on execution or unexecution of instillation of a mydriatic is connected to the input detection unit 32. The third input unit 51 may be disposed on the operation panel C, or may be disposed on a not-shown externally connected information apparatus such as a personal computer.

Figure 7:
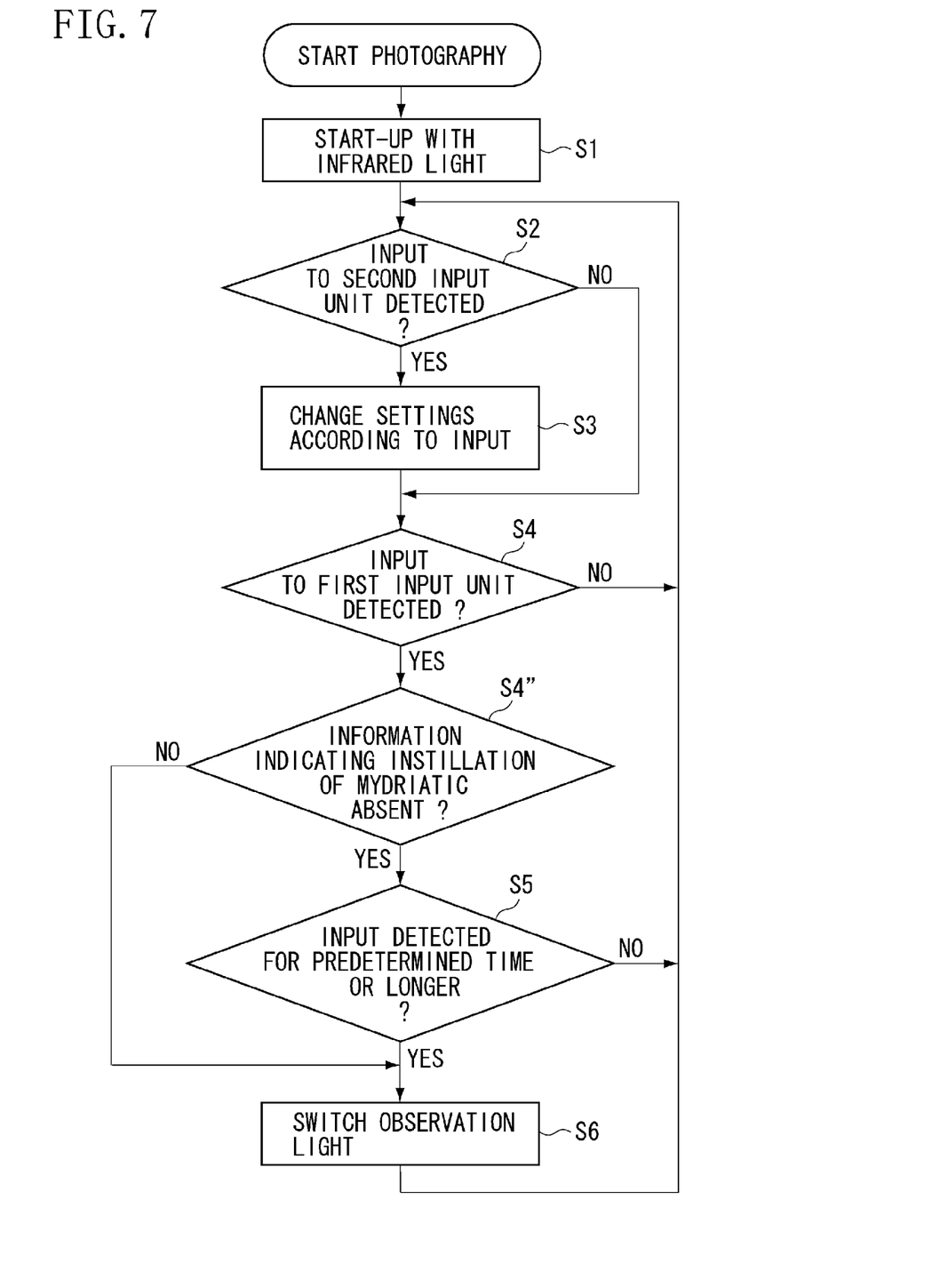
FIG. 7 is an operational flowchart according to the second exemplary embodiment.

FIG. 7 is an operational flowchart according to the second exemplary embodiment. This flowchart includes step S4" newly added to the operational flowchart of the first exemplary embodiment illustrated in FIG. 4. In step S4", the system control unit 31 determines whether the first input unit should be operated for the predetermined time or longer for switching the objection light, based on the information indicating execution or unexecution of instillation of a mydriatic output from the third input unit 51. If it is determined that instillation of a mydriatic is absent (YES in step S4"), similarly to the first exemplary embodiment, the processing proceeds to step S5, and the first input unit should be long-pressed or operated multiple times for switching the observation light.

On the other hand, if it is determined that instillation of a mydriatic is executed (NO in step S4"), the processing proceeds to step S6, and in this case, miosis of the subject's eye E does not occur from an operational mistake regardless of whether the operation mode is switched from the visible light observation to the infrared light observation or from the infrared light observation to the visible light observation. Therefore, the system control unit 31 does not take the route passing through step S5 where determination regarding the predetermined time is performed, and then switches the observation light in step S6. Due to omission of the determination in step S5, the operation can obtain the same operability for the first input unit as the operability of the second input unit, and can avoid having an uncomfortable feeling.

If the input information from the third input unit 51 indicates that a mydriatic is instilled into the subject's eye E, the detection time for the first input unit is changed to be same as the detection time for the second input unit. Due to this arrangement, the operator does not have to operate the first input unit for or within the predetermined time set in the first exemplary embodiment for switching the observation light, and can switch the observation light by operating the first input unit in a similar manner to the operation of the second input unit.

Figure 8:
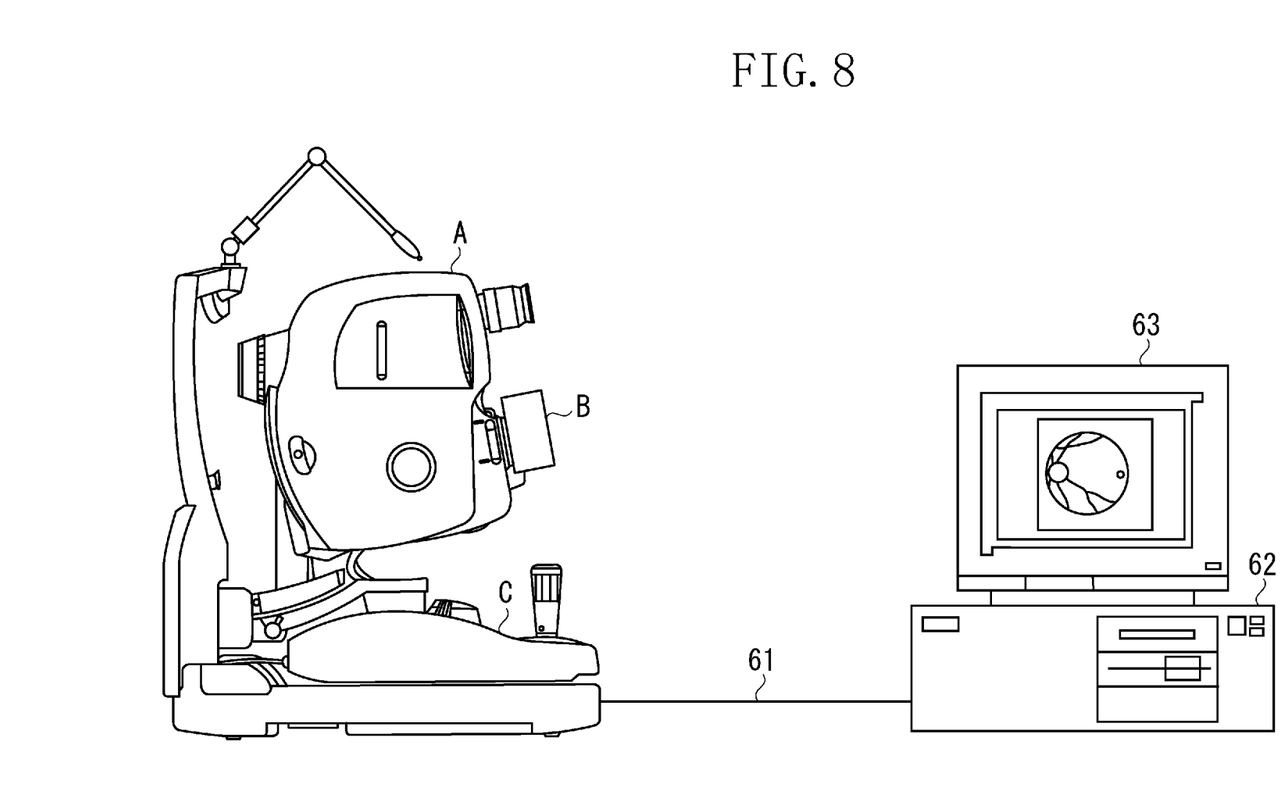
FIG. 8 illustrates a configuration of an ophthalmologic photographing apparatus according to a third exemplary embodiment of the present invention.

FIG. 8 illustrates a configuration of an ophthalmologic photographing apparatus according to a third exemplary embodiment of the present invention. The fundus camera unit A is connected to an external personal computer 62 via a control cable 61. An external monitor 63 is connected to the personal computer 62. An operator can control the system control unit 31 in the fundus camera unit A directly from the personal computer 62.

The personal computer 62 includes a multiple-examination management unit for controlling a plurality of examinations including a visible light observation and an infrared light observation, and manages photography information of a plurality of subjects.

Figure 9:
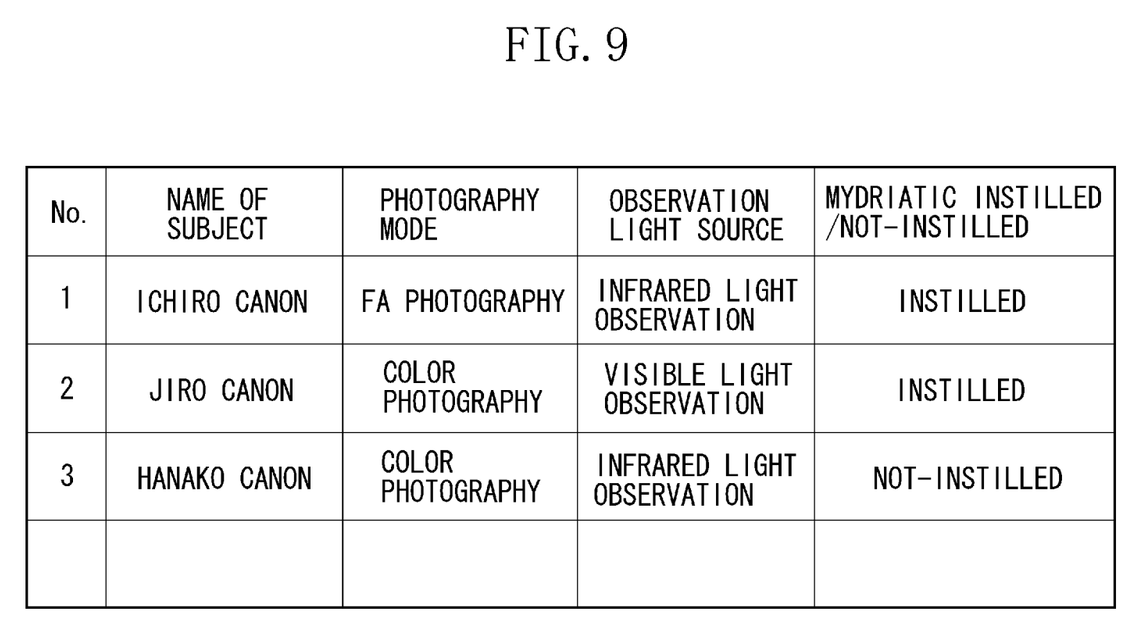
FIG. 9 illustrates a list including photography information of a plurality of subjects.

As illustrated in FIG. 9, the photography information includes, for example, photography mode information indicating various photography modes such as the color photography mode and the fluorescein angiography (FA) (visible fluorescence) photography mode, a selection of the observation light source, information indicating whether the subject's eye E is a left eye or right eye, and information indicating whether a mydriatic is instilled.

The multiple-examination management unit includes the function enabling the various functions of the fundus camera unit A to be changed to the settings according to the selected photography mode from the outside of the fundus camera unit A, based on the pre-input information such as the photograph mode and the information indicating whether a mydriatic is instilled. For example, referring to FIG. 9, subject No. 1 will undergo FA photography under an infrared light observation, and when an operator selects the FA photography of subject No. 1 at the multiple-examination management unit, a control signal is transmitted from the multiple-examination management unit to the system control unit 31. Then, the fundus camera unit A selects a filter for FA photography from not-shown various photography filters. Further, the visible light cut filter 3 is positioned in the optical path, and the infrared light cut filter 11 is retracted from the optical path, thereby completing preparation for executing the infrared light observation.

The operator can also use the observation light changeover switch 43 and the various photography mode switches disposed on the operation panel C. Therefore, both of the switches disposed on the operation panel C and the multiple-examination management unit mounted in the external personal computer 62 can switch the photography mode and the observation light of the fundus camera unit A independently from each other. Therefore, if the switches on the operation panel C are self-holding type switches such as alternate-type switches or slide switches, they may become inconsistent with the setting signals from the multiple-examination management unit. For preventing this problem, the switches on the operation panel C should be automatic-return-type momentary switches such as tactile switches.

Referring to FIG. 9, the FA photography selected for subject No. 1 is characterized in that it takes a long time for each photography since it includes a diagnosis of a lesion area. Further, in this examination, the fundus image required for the diagnosis is images taken in the early stage and the later stage of the FA photography. Therefore, the photography of subject No. 2 and subject No. 3 can be performed during the examination of subject No. 1.

Therefore, after the operator acquires the required image of subject No. 1 in the early stage of the FA photography, the operator gives subject No. 1 a temporary break. Then, successively, the operator selects subject No. 2 at the multiple-examination management unit to perform the photography of subject No. 2. Subject No. 2 should have a mydriatic instilled to his/her eye, and will undergo a visible light observation. The corresponding information is transmitted from the multiple-examination management unit to the system control unit 31, and the system settings are changed to the settings of a visible light observation state.

In conventional control methods, system settings are changed when system information is transmitted from the multiple-examination management unit to the system control unit 31. Therefore, there is a possibility that instillation of a mydriatic to the eye of subject No. 2 may be forgotten, which may cause a situation that visible light is projected to the eye of subject No. 2 without a mydriatic instilled therein. There is another possibility that a mistake in the photography order may cause a situation that visible light is projected to subject No. 3 as a subject's eye E with a mydriatic instilled therein. Therefore, the third exemplary embodiment of the present invention includes an observation light switching warning unit for notifying an operator of a change in the observation light in advance so that it becomes possible to prevent visible light from being projected unintentionally to a subject's eye E without a mydriatic instilled therein by a mistake or carelessness of the operator.

Figure 10:
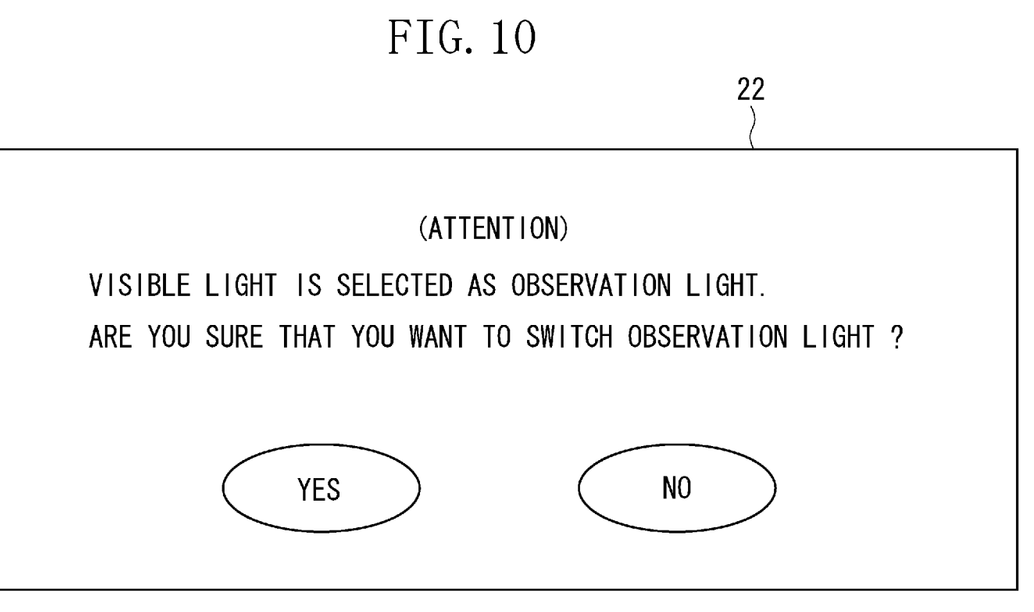
FIG. 10 illustrates a warning state of a liquid crystal monitor.

As illustrated in FIG. 10, an output from the observation light switching warning unit can be displayed at the liquid crystal monitor 22 of the camera body B or a display monitor connected to the personal computer 62. Further, although the warning from the observation light switching warning unit is a function required when the observation mode is switched from the infrared light observation to the visible light observation, a warning may be also issued when the observation mode is switched from the visible light observation to the infrared light observation for the purpose of calling the operator's attention.

After the operator views the observation light switching warning output at the screen, if the operator agrees with the observation light switching, the operator selects "YES" illustrated in FIG. 10, which causes the observation light to be switched. If the operator disagrees with the observation light switching, the operator selects "NO". Then, it is possible to prevent visible light from being projected to the subject's eye E.

In this way, when multiple examinations including a visible light observation and an infrared light observation are conducted at a time, an output of a warning to an operator at the time of switching of the observation light can prevent miosis of a subject's eye that might be otherwise caused by projection of visible light to the subject's eye due to an operator's operational mistake when an infrared light observation without instillation of a mydriatic is intended actually.

Aspects of the present invention can also be realized by a computer of a system or apparatus (or devices such as a CPU or MPU) that reads out and executes a program recorded on a memory device to perform the functions of the above-described embodiment (s), and by a method, the steps of which are performed by a computer of a system or apparatus by, for example, reading out and executing a program recorded on a memory device to perform the functions of the above-described embodiment (s). For this purpose, the program is provided to the computer for example via a network or from a recording medium of various types serving as the memory device (e.g., computer-readable medium).

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2009-196999 filed Aug. 27, 2009, which is hereby incorporated by reference herein in its entirety.

What is claimed is:

1. An ophthalmologic photographing apparatus comprising:
    an illumination unit configured to illuminate a subject's eye with one of infrared light and visible light;
    an input unit configured to input a signal to the illumination unit;
    a measurement unit configured to measure an input time of the signal from the input unit;
    a detection unit configured to detect that the input time is a predetermined time or longer; and
    a control unit configured to control the illumination unit according to a detection result by the detection unit to switch from the infrared light to the visible light.

2. The ophthalmologic photographing apparatus according to claim 1, wherein the input time includes a time for which the signal is continuously or intermittently input from the input unit.

3. The ophthalmologic photographing apparatus according to claim 1, wherein the input unit includes a switch, and
    wherein the input time includes a time for which the signal is continuously input by a long-press of the switch, or a time for which the signal is intermittently input by a plurality of presses of the switch.

4. The ophthalmologic photographing apparatus according to claim 3, wherein the predetermined time is set longer than a time set to a switch other than the input unit.

5. The ophthalmologic photographing apparatus according to claim 1, wherein the predetermined time is set longer than a time set for switching from the visible light to the infrared light.

6. The ophthalmologic photographing apparatus according to claim 1, wherein the illumination unit comprises:
    an infrared light observation unit for observing the subject's eye with the infrared light; and
    a visible light observation unit for observing the subject's eye with the visible light, and
    wherein the control unit controls the infrared light observation unit and the visible light observation unit according to the detection result by the detection unit.

7. The ophthalmologic photographing apparatus according to claim 1, further comprising a notification unit configured to notify an operator of switching from the infrared light to the visible light.

8. An ophthalmologic photographing method comprising:
measuring an input time of a signal input into an illumination unit configured to illuminate a subject's eye with one of infrared light and visible light; and
controlling the illumination unit according to a result of detection that the input time is a predetermined time or longer to switch from the infrared light to the visible light.

9. A computer-readable storage medium storing a program for causing a computer to execute the ophthalmologic photographing method according to claim 8.

10. An ophthalmologic photographing apparatus comprising:
an illumination unit configure to illuminate a subject's eye with one of infrared light and visible light;
a switch configured to receive input from an operator;
a measurement unit configured to measure a time during which the switch is being pressed; and
a control unit configured to control the illumination unit and change light with which the subject's eye is illuminated from the infrared light to the visible light, in a case where the time during which the switch is being pressed measured by the measurement unit is determined to be a predetermined time or longer.

11. An ophthalmologic apparatus comprising:
a first switch configured to issue an instruction to switch light for illuminating a subject's eye between infrared light and visible light;
a second switch configured to issue an instruction to select fluorescence photography or color photography,
wherein a time to keep the first switch pressed for switching light for illuminating the subject's eye from infrared light to visible light is longer than a time to keep the second switch pressed for selecting fluorescence photography or color photography.

12. The ophthalmologic apparatus according to claim 11, wherein the time to keep the first switch pressed for switching the light for illuminating the subject's eye from infrared light to visible light is longer than a time to keep the first switch pressed for switching the light for illuminating the subject's eye from visible light to infrared light.

13. The ophthalmologic apparatus according to claim 11, wherein the time to keep the first switch pressed for switching the light for illuminating the subject's eye from infrared light to visible light is equal to or longer than a predetermined time.

14. The ophthalmologic apparatus according to claim 11, further comprising a switch unit configured to switch the light for illuminating the subject's eye from infrared light to visible light in a case where the time to keep the first switch pressed is equal to or longer than a predetermined time.

15. The ophthalmologic apparatus according to claim 14, further comprising:
a light source configured to emit illumination light including infrared light and visible light;
a first filter disposed in such a way as to be inserted into and retracted from an optical path connecting the light source and the subject's eye, and configured to restrict visible light from entering the subject's eye; and
a second filter disposed in such a way as to be inserted into and retracted from the optical path, and configured to restrict infrared light from entering the subject's eye,
wherein the switch unit switches the light for illuminating the subject's eye from infrared light to visible light by retracting the first filter from the optical path and inserting the second filter into the optical path.

16. The ophthalmologic apparatus according to claim 11, further comprising a control unit configured to switch the light for illuminating the subject's eye from infrared light to visible light in a case where the time to keep the first switch pressed is equal to or longer than a first predetermined time, and to select fluorescence photography or color photography in a case where the time to keep the second switch pressed is equal to or longer than a second predetermined time that is shorter than the first predetermined time.

17. An ophthalmologic apparatus comprising:
a switch configured to issue an instruction to switch light for illuminating a subject's eye between infrared light and visible light; and
a change unit configured to change a time to keep the switch pressed for switching light for illuminating the subject's eye from infrared light to visible light based on information indicating whether a mydriatic is instilled or not.

18. The ophthalmologic apparatus according to claim 17, the time to keep the switch pressed for switching light for illuminating the subject's eye from infrared light to visible light is longer in a case where the information indicates that a mydriatic is instilled than in a case where the information indicates that a mydriatic is not instilled.

19. An ophthalmologic apparatus comprising:
a first instruction unit configured to issue an instruction to switch light for illuminating a subject's eye between infrared light and visible light;
a second instruction unit configured to issue an instruction to select fluorescence photography or color photography,
wherein a time to keep the first instruction unit selected for switching light for illuminating the subject's eye from infrared light to visible light is longer than a time to keep the second instruction unit selected for selecting fluorescence photography or color photography.

20. The ophthalmologic apparatus according to claim 19, further comprising:
a switch unit configured to switch the light for illuminating the subject's eye from infrared light to visible light in a case where the time to keep the first instruction unit selected is equal to or longer than a predetermined time;
a light source configured to emit illumination light including infrared light and visible light;
a first filter disposed in such a way as to be inserted into and retracted from an optical path connecting the light source and the subject's eye, and configured to restrict visible light from entering the subject's eye; and
a second filter disposed in such a way as to be inserted into and retracted from the optical path, and configured to restrict infrared light from entering the subject's eye,
wherein the switch unit switches the light for illuminating the subject's eye from infrared light to visible light by retracting the first filter from the optical path and inserting the second filter into the optical path.

* * * * *